United States Patent
Syage et al.

(10) Patent No.: US 8,723,111 B2
(45) Date of Patent: May 13, 2014

(54) APPARATUS FOR CHEMICAL SAMPLING AND METHOD OF ASSEMBLING THE SAME

(75) Inventors: Jack A. Syage, Corona del Mar, CA (US); Kaveh Jorabchi, Arlington, VA (US)

(73) Assignee: Morpho Detection, LLC, Newark, CA (US)

( * ) Notice: Subject to any disclaimer, the term of this patent is extended or adjusted under 35 U.S.C. 154(b) by 52 days.

(21) Appl. No.: 13/248,501

(22) Filed: Sep. 29, 2011

(65) Prior Publication Data
US 2013/0082172 A1  Apr. 4, 2013

(51) Int. Cl.
*H01J 49/14* (2006.01)

(52) U.S. Cl.
USPC .......... 250/288; 250/282; 250/423 P

(58) Field of Classification Search
USPC .......... 250/281, 282, 288, 289, 423 P
See application file for complete search history.

(56) References Cited

U.S. PATENT DOCUMENTS

| | | | |
|---|---|---|---|
| 5,968,837 A | 10/1999 | Doring et al. | |
| 6,211,516 B1 | 4/2001 | Syage et al. | |
| 6,225,623 B1 * | 5/2001 | Turner et al. | 250/286 |
| 6,329,653 B1 | 12/2001 | Syage et al. | |
| 6,534,765 B1 * | 3/2003 | Robb et al. | 250/288 |
| 6,630,664 B1 | 10/2003 | Syage et al. | |
| 6,949,741 B2 | 9/2005 | Cody et al. | |
| 7,015,466 B2 | 3/2006 | Takats et al. | |
| 7,112,785 B2 | 9/2006 | Laramee et al. | |
| 7,119,342 B2 | 10/2006 | Syage et al. | |
| 7,161,144 B2 | 1/2007 | Syage et al. | |
| 7,196,325 B2 | 3/2007 | Syage | |
| 7,196,525 B2 | 3/2007 | Sparkman et al. | |
| 7,700,913 B2 | 4/2010 | Musselman | |
| 7,706,297 B1 | 4/2010 | Venkatraman | |
| 7,714,281 B2 | 5/2010 | Musselman | |
| 2008/0048107 A1 | 2/2008 | Mcewen | |
| 2009/0152458 A1 * | 6/2009 | Vilkov et al. | 250/282 |
| 2009/0159790 A1 * | 6/2009 | Kostiainen et al. | 250/282 |
| 2011/0049352 A1 * | 3/2011 | Ding et al. | 250/282 |
| 2011/0272571 A1 * | 11/2011 | Kenttamaa et al. | 250/282 |
| 2011/0281372 A1 * | 11/2011 | Atkinson et al. | 436/174 |
| 2012/0037797 A1 * | 2/2012 | Li et al. | 250/282 |

OTHER PUBLICATIONS

Cody et al., "Versatile New Ion Source for the Analysis of Materials in Open Air under Ambient Conditions", Anal. Chem. 2005, 77, 2297-2302.*

Cody et al, "Versatile New Ion Source for the Analysis of Materials in Open Air under Ambient Conditions", Anal Chem. 2005, 77, 2297-2302.*

Kafui Kpegba, et al., Analysis of Self-Assembled Monolayers on Gold Surfaces Using Direct Analysis in Realtime Mass Spectrometry, Analytical Chemistry, 2007, pp. 5479-5483, vol. 79, No. 14, American Chemical Society.

(Continued)

*Primary Examiner* — Jack Berman
*Assistant Examiner* — David E Smith
(74) *Attorney, Agent, or Firm* — Armstrong Teasdale LLP

(57) ABSTRACT

A chemical sampling system includes a direct analysis in real time (DART) device and an atmospheric pressure photoionization (APPI) device positioned proximate the DART device. Another chemical sampling system includes the APPI device positioned proximate to a thermal desorption device.

24 Claims, 13 Drawing Sheets

(56) References Cited

OTHER PUBLICATIONS

Charles N. McEwen, et al., Analysis of Solids, Liquids, and Biological Tissues Using Solids Probe Introduction at Atomspheric Pressure on Commercial LC/MS Instruments, Analytical Chemistry, 2005, pp. 7826-7831, vol. 77, No. 23, American Chemical Society.

Robert B. Cody, et al., Versatile New Ion Source for the Analysis of Materials in Open Air Under Ambient Conditions, Analytical Chemistry, 2005, pp. 2297-2302, vol. 77, No. 8, American Chemical Society.

Olivier P. Haefliger and Nicolas Jeckelmann, Direct Mass Spectrometric Analysis of Flavors and Fragrances in Real Applications using Dart, Rapid Communications in Mass Spectrometry, 2007, pp. 1361-1366, vol. 21, Wiley InterScience.

Jonathan P. Williams, et al., The use of Recently Described Ionisation Techniques for the Rapid Analysis of Some Common Drugs and Samples of Biological Origin, Rapid Communications in Mass Spectrometry, 2006, pp. 1447-1456, vol. 20, Wiley InterScience.

Gertrud Morlock and Yoshihisa Ueda, New Coupling of Planar Chromatography with Direct Analysis in Real Time Mass Spectrometry, Journal of Chromatography A, 2007, pp. 243-251, vol. 1143, Science Direct, Elsevier.

\* cited by examiner

Table – Signal area and (%RSD)

| Compound | He - DART | He - APPI/DART | N₂ – APPI/DART |
|---|---|---|---|
| [Aldicarbsulfone+H]⁺ | 4.77E+04 (20%) | 2.27E+05 (20%) | 1.29E+05 (13%) |
| [Estradiol]⁺ | 4.03E+03 (59%) | 1.03E+05 (10%) | 5.32E+04 (23%) |
| [Estradiol-OH]⁺ | 4.45E+04 (10%) | 2.24E+05 (17%) | 2.42E+04 (24%) |
| [Cortisol+H]⁺ | 7.86E+04 (38%) | 2.46E+05 (20%) | 3.60E+05 (51%) |
| [Verapamil+H]⁺ | 7.09E+04 (12%) | 5.28E+05 (7%) | 2.59E+06 (11%) |

FIG. 7

APPARATUS FOR CHEMICAL SAMPLING AND METHOD OF ASSEMBLING THE SAME

BACKGROUND OF THE INVENTION

The embodiments described herein relate generally to chemical analysis systems and, more particularly, to detecting chemicals using atmospheric pressure photoionization with direct analysis in real time and thermal desorption.

Most known ambient analysis methods and apparatus include a means to analyze chemical compositions directly from surfaces and objects without the need for sample preparation. There are many applications for ambient analysis in a wide range of fields such as toxic and non-toxic chemical compound contamination and sensing, pathogen and toxin diagnostics, environmental monitoring of pollutants, detection and control of chemical processes, and clinical analysis of urine and blood samples.

Some known ambient analysis methods and apparatus include a means to desorb and ionize analyte samples on surfaces and objects using a gaseous stream of metastable atoms such as helium, argon, or molecules such as nitrogen. The metastable gaseous stream is formed by passing the gases through a discharge region. The discharge also causes a heating of the gas, which may be supplemented with direct heating, and helps to desorb molecules from objects into the vapor phase, i.e., a flowing afterglow discharge, where they can then ionize by Penning ionization from the metastable gases. These resultant vapor phase ions can then be sampled by a mass spectrometer or other ion analysis method. This method is called direct analysis in real time (DART).

Another known ambient analysis method and apparatus is called desorption electrospray ionization (DESI), wherein an electrospray ionization (ESI) source is aimed at objects and surfaces that may have compounds adhered thereon. The ESI source impinges on the surface and a process of surface molecule ionization and ion desorption occurs. As with DART, these resultant vapor phase ions can then be sampled by a mass spectrometer or other ion analysis method.

Yet another known ambient analysis method and apparatus includes inserting a liquid or other sample into a sampling tube or capillary and then inserting the sample into a heating element. The sample can then vaporize and be ionized by a variety of atmospheric pressure ionization sources including an atmospheric pressure chemical ionization (APCI) source and/or photoionization including atmospheric pressure photoionization (APPI). Generally, photoionization produces a positively charged ion. This occurs because the absorption of a photon by a molecule can lead to dissociation of an electron. However, the generation of these electrons may also lead to negative ion formation by a number of possible mechanisms, such as electron attachment, dissociative electron attachment, and deprotonation. The generation of electrons can be enhanced by putting a high abundance of photoionizable compounds called dopants into the vapor phase. Dopants can also lead to an enhanced yield of positive ions since the positive dopant ions can react with neutral vapor molecules by charge transfer or proton transfer. Dopants may include, for example, toluene, benzene, chloro-benzene, acetone, anisole or a combination of these compounds or other compounds, which tend to be liquids and are then vaporized. Dopants may be used with methods that include ion mobility spectrometry, or ion mass spectrometry.

Each of these ambient analysis methods has specific benefits for specific applications. For example DART is most useful for rapidly screening large areas, whereas, in contrast, DESI is most useful for screening small areas, and therefore DESI is typically used to image the chemical compositions on surfaces and objects. However, these methods also have some key disadvantages that limit their applicability and utility. For example, the ionization methods of ESI and DART have limitations on the range of compounds that can be ionized, wherein non-polar molecules, such as petroleum compounds, polyaromatic hydrocarbons, pesticides, steroids, and lipids, may be weakly detected, or undetected altogether.

Also, ESI and DART ionization methods are based on, or at least are strongly dependent upon, ion-molecule type reactions, and are therefore susceptible to ion and matrix suppression due to competition for charge, particularly in those samples that are not prepared or cleaned up. DART does not operate well with air because the presence of oxygen degrades the discharge process needed to create a metastable gas flow. Therefore, to use DART, process gases must be purchased and stored. Further, DART tends to work best with helium gas. To reduce costs, DART may be adapted to use less expensive nitrogen gas. However, this leads to formation of metastable nitrogen molecules for ionization, wherein such metastable nitrogen is not nearly as effective as metastable helium.

BRIEF SUMMARY OF THE INVENTION

In one aspect, a chemical sampling system is provided. The sampling system includes a direct analysis in real time (DART) device. The system also includes an atmospheric pressure photoionization (APPI) device positioned proximate to the DART device.

In another aspect, a chemical sampling system is provided. The sampling system includes a thermal desorption device. The system also includes an atmospheric pressure photoionization (APPI) device positioned proximate to the thermal desorption device.

In yet another aspect, a method of assembling a sampling system is provided. The method includes providing an atmospheric pressure photoionization (APPI) device. The method also includes positioning at least one of a direct analysis in real time (DART) device and a thermal desorption device in close proximity to the APPI device.

BRIEF DESCRIPTION OF THE DRAWINGS

FIG. 7 is a tabular view of comparisons of signal levels and percent relative standard deviations (% RSD) for a variety of compounds and a variety of analysis methods;

DETAILED DESCRIPTION OF THE INVENTION

The embodiments described herein include an ambient analysis sampling and detection system that enables direct chemical analysis in real time of samples either in their natural environment or deposited on object surfaces and/or convenient sample substrates. Specifically, some of the particular embodiments of sampling systems described herein enhance the performance of a flowing afterglow discharge method referred to as direct analysis in real time (DART) by adding an atmospheric pressure photoionization (APPI) device, an associated dopant flow, and predetermined geometric constraints to form desired ions and facilitate their transmission into an ion analyzer, such as a mass spectrometer. More specifically, in such sampling systems, DART and APPI are combined to increase the effectiveness of DART-based sampling systems in detecting and analyzing a greater number of substances and/or compounds. Also, more specifically, APPI is based on the direct method of photon absorption by a molecule to induce ionization thereof, and is therefore significantly less subject to charge affinities or the suppression effects of ion-molecule reactions. Furthermore, the integration of APPI with DART significantly increases a sampling system-generated ionization signal relative to DART alone, including those compounds that are well detected by DART.

Also, specifically, some of the sampling systems disclosed herein do not use DART and the associated afterglow discharge. Rather, such sampling systems use a heated gas flow to desorb the sample and then use APPI to ionize the vaporized neutral analyte sample. Such apparatus and methods use air rather than purified cylinder gases, such as helium, argon, or nitrogen, thereby improving operational convenience for in-field use and reducing the costs of procuring and storing such purified cylinder gases.

Further, specifically, although DART tends to not work well with air and tends to work best with helium gas, APPI does not require metastable gases and APPI works equally well with helium and nitrogen. Moreover, APPI operates well in the presence of any common gas, such as ambient air. In this case normal air can be flowed through a heater and used to desorb sample molecules which are then ionized by APPI.

Figure 1:
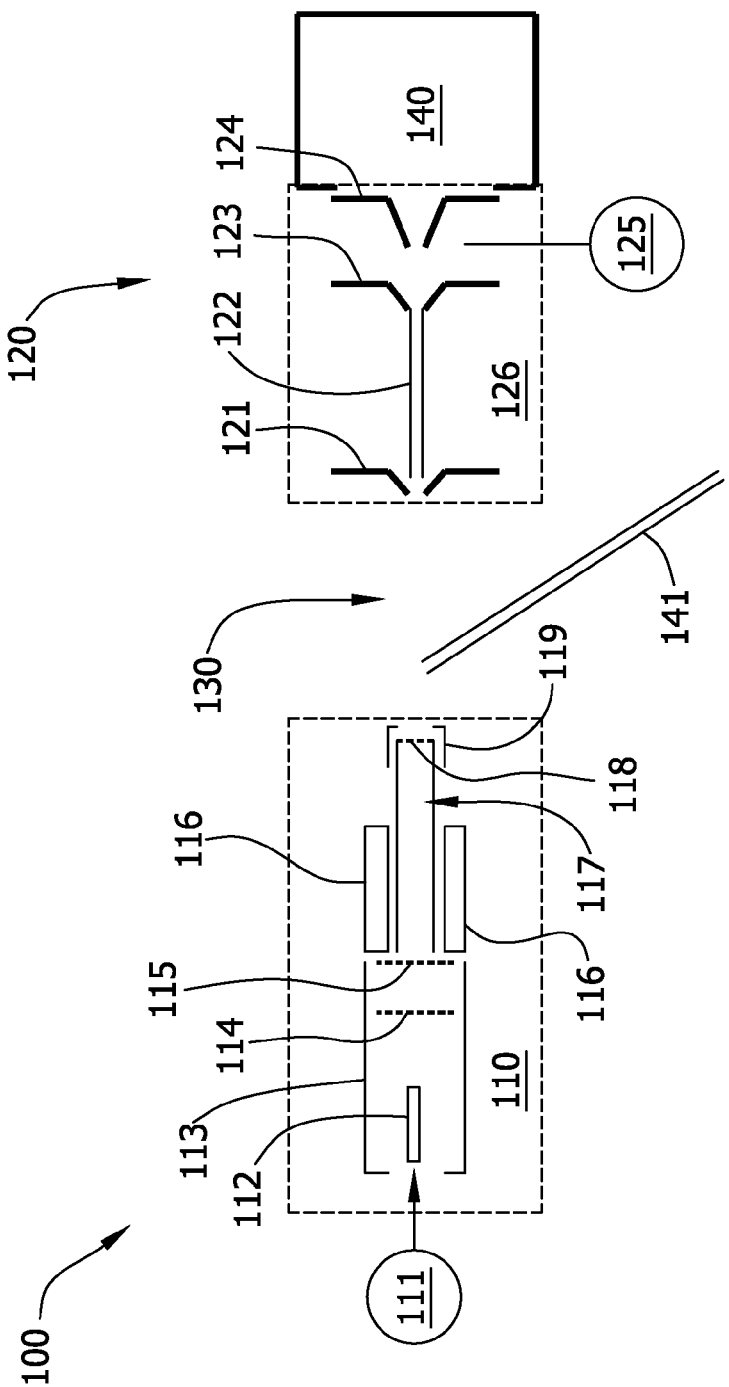
FIG. 1 is a schematic view of a prior art ambient analysis system using direct analysis in real time (DART)

FIG. 1 is a schematic view of a prior art ambient analysis system 100 using direct analysis in real time (DART). Ambient analysis system 100 includes a DART device 110 and a flow of purified gas 111 that is typically helium or nitrogen. A needle electrode 112 and a downstream ground grid electrode 114 causes a discharge that creates a flowing afterglow discharge, i.e., a plasma (not shown) of electrically-excited metastable and ionized gas that is channeled to an electrode 115 downstream of electrode 114. Electrodes 112, 114, and 115 are positioned in an electrode housing 113.

The gas plasma flows into a region 117 defined longitudinally between electrode 115 and another downstream electrode 118, and defined radially by a plurality of heaters 116. Electrode 115 facilitates the removal of the ions and retaining the metastable gas in a neutral condition. The gas is further heated by heaters 116 and is channeled to electrode 118 that further facilitates the removal of the ions and retaining the metastable gas in a neutral condition. The substantially neutral, heated, metastable gas exits DART device 110 and is channeled through an insulator cap 119 into a sample region 130.

The substantially neutral, heated, metastable gas then impinges on a sample that includes, without limitation, an object, a surface, and a substrate. For illustration purposes, the sample object is a capillary tube 141. The substantially neutral, heated, metastable gas acts to desorb and ionize compounds (not shown) on the sample surface (not shown) of capillary tube 141 and these compounds are drawn into an ion detector 120 for analysis. Ion detector 120 includes an ion vacuum interface 126 that is at least partially defined by an entrance cone 121, an ion sampling tube, e.g., an ion transmission capillary 122, and a low pressure plate 123. Ion detector 120 also includes a skimmer aperture 124 that couples ion vacuum interface 126 in flow communication with a mass spectrometer or mass spectra analyzer, e.g., a high vacuum ion mass analyzer 140. Ion detector 120 further includes a pump 125 that draws most of the substantially neutral, heated, metastable gas thereby facilitating an enriched ion flow through skimmer aperture 124 into ion mass detector 140.

Figure 2:
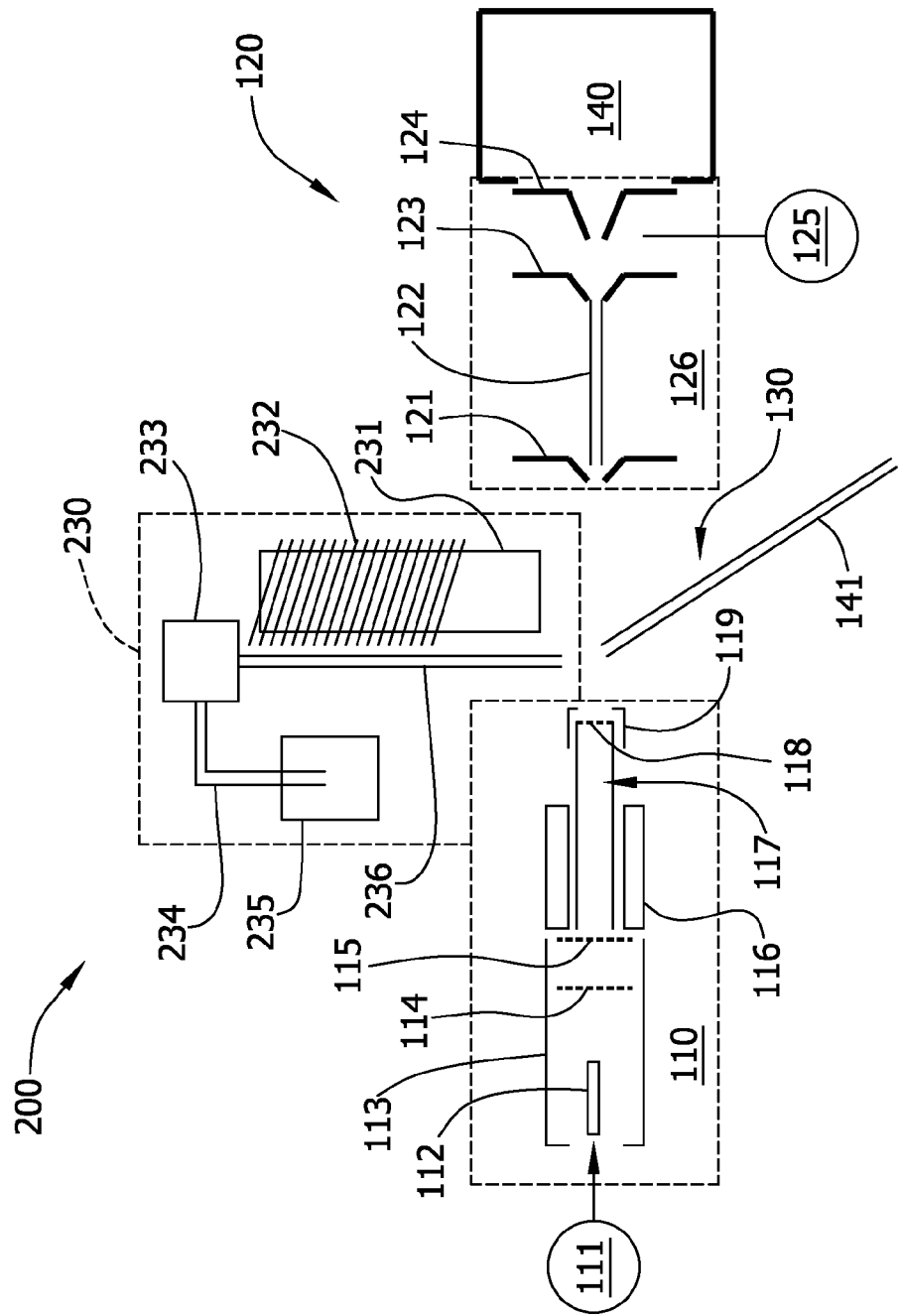
FIG. 2 is a schematic view of an exemplary sampling system that includes an exemplary atmospheric pressure photoionization (APPI) device operatively coupled to ambient analysis system 100 using DART (shown in FIG. 1)

FIG. 2 is a schematic view of an exemplary sampling system 200 that includes an exemplary atmospheric pressure photoionization device 230 operatively coupled to ambient analysis system 100 that includes DART device 110. Atmospheric pressure photoionization (APPI) device 230 provides a supplemental ionization mechanism to that provided by the metastable gas flow produced by DART device 110. APPI device 230 includes a vacuum ultraviolet light source 231 driven by a source housing 232, that in the exemplary embodiment is a coil that creates a radiofrequency discharge plasma (not shown) in light source 231. The resultant photons generated by light source 231 are of sufficient energy to ionize most types of sample compounds of interest. DART device 110 and APPI device 230 are shown in FIG. 2 as oriented at approximately 90° with respect to each other. Alternatively, DART device 110 and APPI device 230 are oriented at any angle with respect to each other that enables operation of sampling system 200 as described herein.

In the exemplary embodiment, photoionization device 230 also includes a supplemental flow of liquid or gas that includes compounds that are readily ionized by light source 231, such supplemental flow of liquid or gas is typically referred to as a dopant. Therefore, sampling system 200 includes a reservoir 235 of such supplemental mixture and a dopant pump 233 coupled in flow communication with reservoir 235 via a dopant transfer line 234. Dopant pump 233 channels the mixture to flow to sample region 130 through a dopant delivery line 236. Typically the dopant sample is a liquid and is vaporized by heaters (not shown) before it enters or as it is entering sample region 130 where capillary tube 141 is positioned. In the exemplary embodiment, direct, or active heating is not needed because the liquid dopant flow is effectively vaporized by the heated metastable gas channeled from DART device 110. Photoionization device 230 has significant benefits over DART device 110 alone and augments the ionization efficiency of DART device 110 (discussed further below).

Also, in the exemplary embodiment, dopant delivery line 236 is shown substantially parallel to light source 231 and source housing 232. Alternatively, dopant delivery line 236 may be oriented at any angle with respect to light source 231 and source housing 232 that enables operation of sampling system 200 as described herein.

Figure 3:
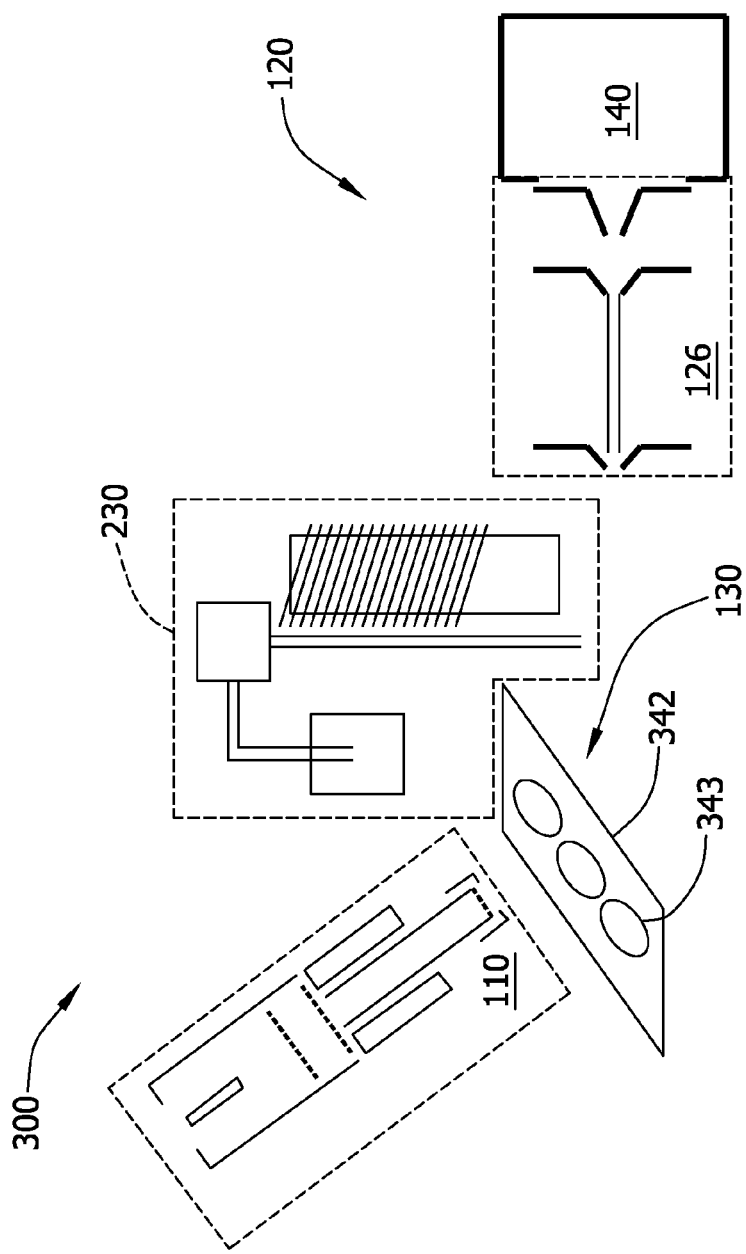
FIG. 3 is a schematic view of an exemplary alternative sampling system.

FIG. 3 is a schematic view of an exemplary alternative sampling system 300. In this exemplary alternative embodiment, sampling system 300 includes DART device 110, photoionization device 230, and ion detector 120. Also, in this alternative embodiment, DART device 110 is oriented at an angle to facilitate analyzing a variety of samples such as an array of samples 343 deposited on a translatable sample substrate 342. Some alternate embodiments include DART 110, photoionization device 230, and ion detector 120 oriented and configured to analyze a liquid sample stream (not shown).

Figure 4:
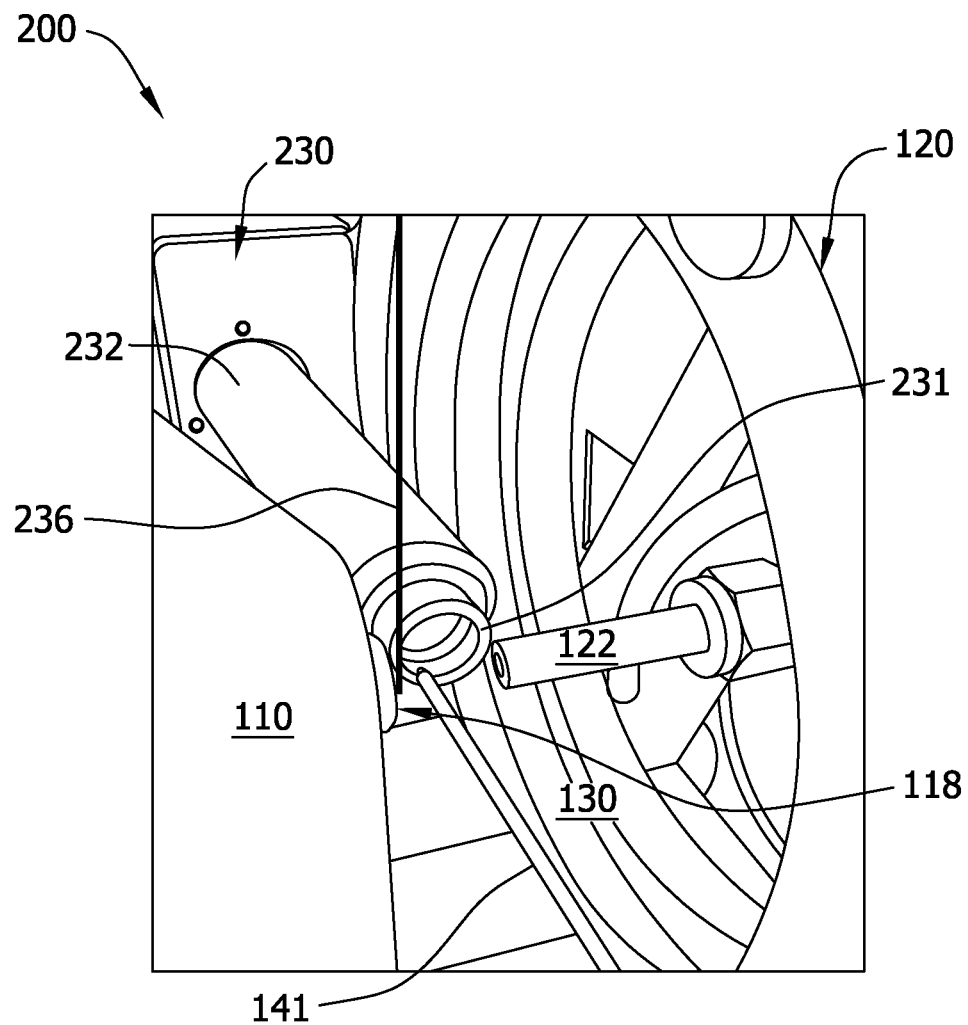
FIG. 4 is a schematic perspective view of a portion of the sampling system shown in FIG. 2.

FIG. 4 is a schematic perspective view of a portion of sampling system 200. In the exemplary embodiment, a sample including approximately 6 nanograms of the compound anthracene (not shown) is deposited on capillary tube 141. Also, in the exemplary embodiment, dopant delivery line 236 is shown substantially perpendicular to light source 231 and source housing 232. Alternatively, dopant delivery line 236 may be oriented at any angle with respect to light source 231 and source housing 232 that enables operation of sampling system 200 as described herein.

Figure 5:
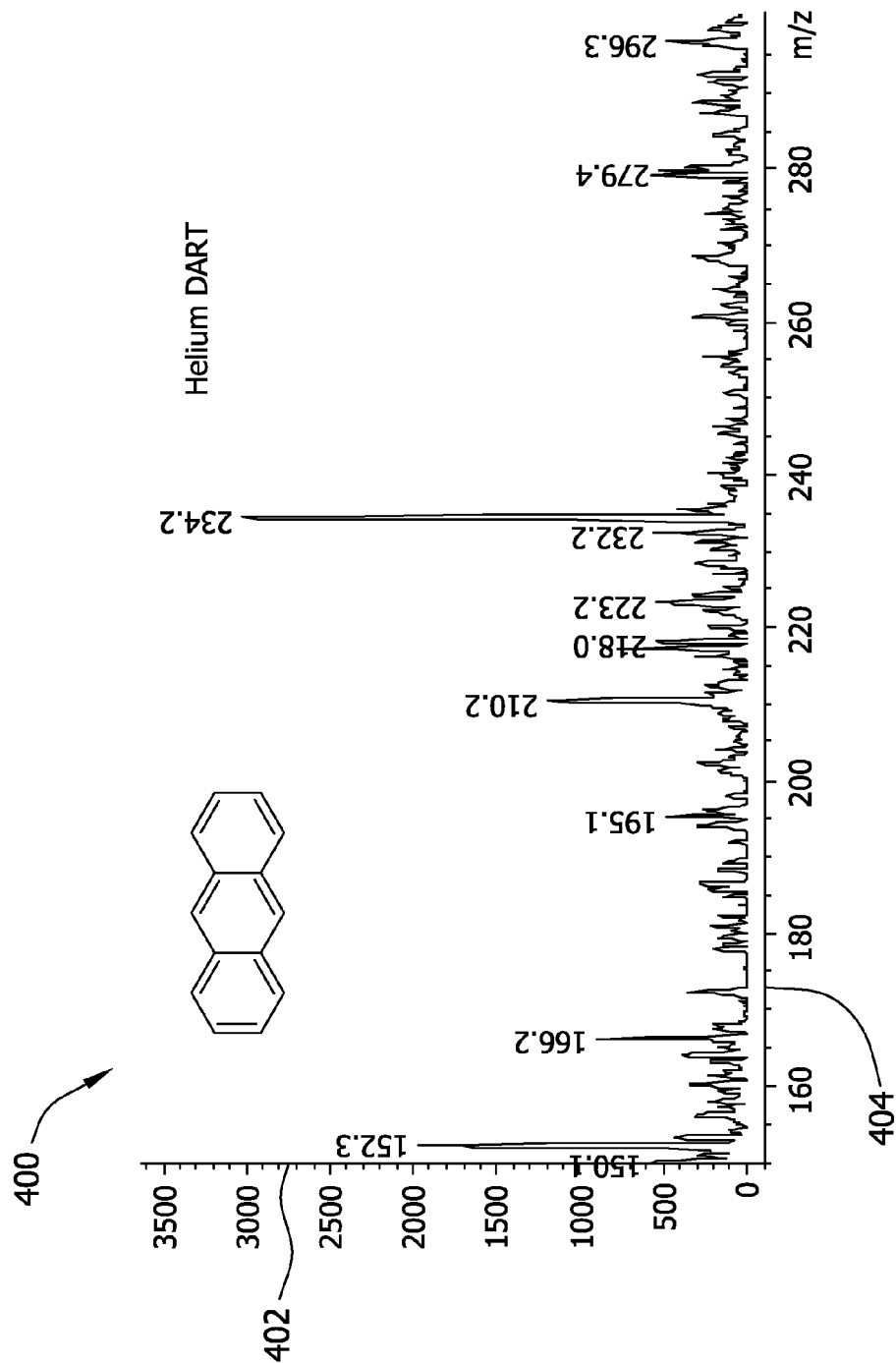
FIG. 5 is a graphical view of a mass spectra analysis of an anthracene sample performed using a sampling system including only standard DART shown in FIG. 1 with helium gas.

FIG. 5 is a graphical view, i.e., graph 400 of a mass spectra analysis of the 6 nanogram sample of the compound anthracene performed using sampling system 100 (shown in FIG. 1) including only standard DART with helium gas. Graph 400 includes an ordinate (y-axis) 402 that represents a signal amplitude in unitless values, such values at least partially represent a relative abundance of the constituents of the compound under analysis. Y-axis 402 is shown in increments of 100 from 0 to 3600. Graph 400 also includes an abscissa (x-axis) 404 that represents a dimensionless mass-to charge (m/z) ratio along a spectrum generated by the compound under analysis. X-axis 404 is shown in increments of 5 from 150 through 300. Graph 400 shows that sample analysis using helium DART, which is more efficient than nitrogen DART, is ineffective at detecting anthracene.

Figure 6:
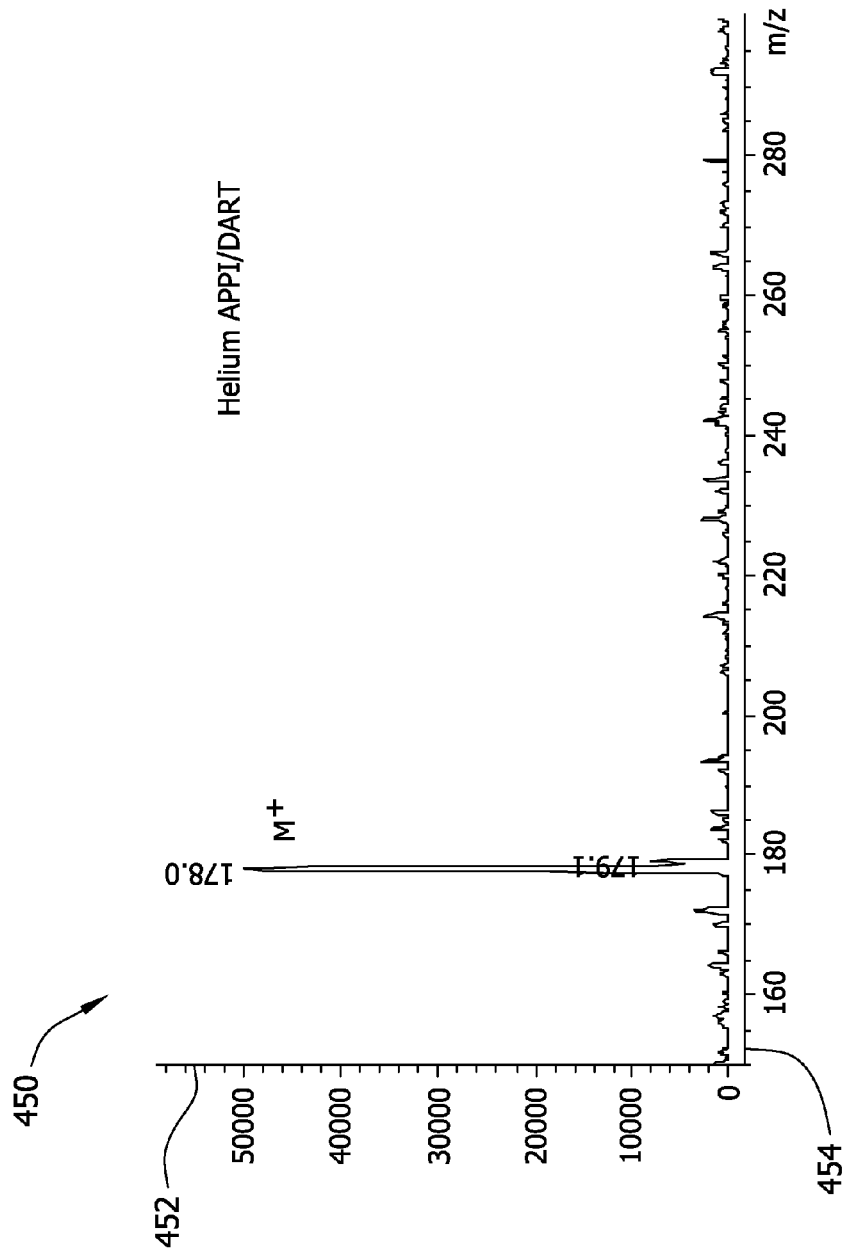
FIG. 6 is a graphical view of a mass spectra analysis of an anthracene sample performed using the sampling system shown in FIG. 4.

FIG. 6 is a graphical view, i.e., graph 450 of a mass spectra analysis of the 6 nanogram sample of the compound anthracene performed using sampling system 200 (shown in FIG. 4). Graph 450 includes an ordinate (y-axis) 452 that represents a signal amplitude in unitless values, such values at least partially represent a relative abundance of the constituents of the compound under analysis. Y-axis 452 is shown in increments of 2000 from 0 to 56,000. Graph 450 also includes an abscissa (x-axis) 454 that represents a dimensionless mass-to charge (m/z) ratio along a spectrum generated by the compound under analysis. X-axis 454 is shown in increments of 5 from 150 through 300.

Referring to FIGS. 4 and 6, in the exemplary embodiment, a dopant flow of approximately 10 microliters a minute of toluene through delivery line 236 is used. FIG. 6 shows a molecular ion peak $M^+$ of anthracene peaking at approximately 50,000 at an m/z ratio of approximately 178, wherein such indication of anthracene is significantly larger than any other constituent in the sample. Therefore, the integrated operation of atmospheric pressure photoionization (APPI) device 230 with DART device 110 (using helium) and ion detector 120 facilitates results that include over an approximately hundred-fold increase in signal for the anthracene constituent in the sample as compared to a similar m/z ratio in FIG. 5.

FIG. 7 is a tabular view, i.e., table 500 of comparisons of signal levels and percent relative standard deviations (% RSD) for a variety of compounds and a variety of analysis methods. A first column 502 includes a variety of compounds. A second column 504 includes the values for helium DART using sampling system 100 (shown in FIG. 1). A third column 506 includes the values for APPI and helium DART using sampling system 200 (shown in FIGS. 2 and 4). A fourth column 508 includes the values for APPI and nitrogen DART using sampling system 200. The values in column 506 are approximately one order of magnitude greater than those in column 504 for each substance, indicating that APPI integrated with helium DART is more effective at identifying substances than merely helium DART alone. Also, values in fourth column 508 are typically greater than those values in column 504 ([Estradiol-OH]$^+$ being the exception), indicating that APPI integrated with nitrogen DART, that is not as effective as helium DART, is also superior to helium DART alone.

Sample system 200 (shown in FIGS. 2 and 4) as described herein, including APPI device 230 not only enhances the ion signal from DART device 110, but the magnitude of the enhancement is sufficiently large that the ionization mechanism associated with DART device 110 may be dispensed with and DART as a sample desorption method only may be used with APPI device 230. This method of operation has the significant benefit that it enhances the choices of flow gases that can be used in system 200. Specifically, for the DART discharge to generate a metastable gas flow, the gas must be absent of oxygen. Such a requirement creates the need for pure gas cylinders or gas purifiers, both increasing the costs of sample analysis. If used only as a thermal desorption source, then ambient air may be used, thereby greatly simplifying the operation and reducing costs of analysis.

Figure 8:
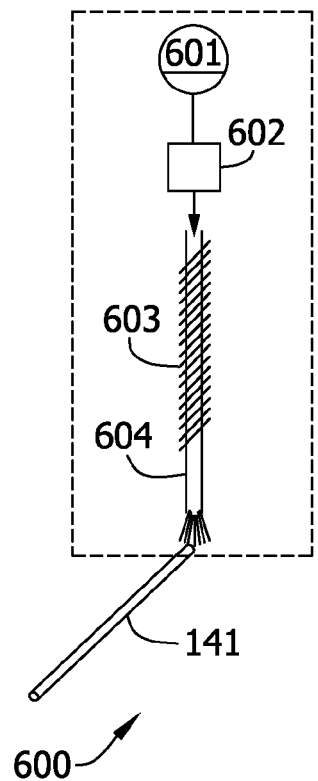
FIG. 8 is a schematic view of an exemplary thermal desorption device that may be used with the sample system shown in FIGS. 2 and 4.

FIG. 8 is a schematic view of an exemplary thermal desorption device 600 that may be used with sample system 200 (shown in FIGS. 2 and 4). Thermal desorption device 600 includes a gas source 601, a gas pump or blower 602 coupled in flow communication with gas source 601, a gas tube 604 coupled in flow communication with pump/blower 602, and at least one heating element 603 extending about tube 604. A heated, pressurized desorption gas flow (not shown) from thermal desorption device 600 impinges on capillary tube sample 141. In the exemplary embodiment, the gas used with device 600 is ambient air. Alternatively, any gas that enables operation of device 600 and sampling system 200 as described herein is used. Some alternative embodiments of thermal desorption device 600 include other fluid delivery means, including, without limitation, dopant delivery devices such as pump 233, transfer line 234, reservoir 235, and delivery line 236 (all shown in FIG. 2) integrated with heating element 603 and tube 604. In the exemplary embodiment, thermal desorption device 600 is used for desorption and/or dopant delivery in place of APPI device 230 (shown in FIG. 2). Other alternative embodiments include APPI device 230 used in addition to thermal desorption device 600.

Figure 9:
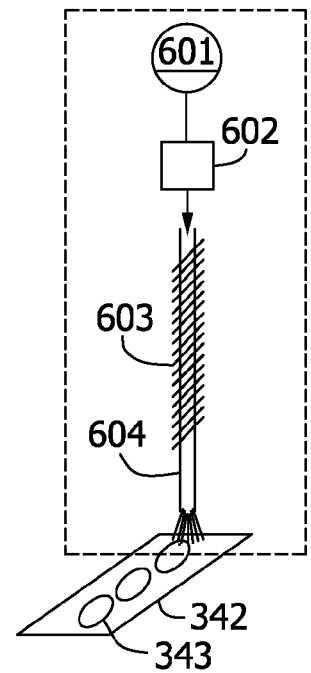
FIG. 9 is a schematic view of an exemplary alternative thermal desorption device that may be used with the sample system shown in FIGS. 2 and 4.

FIG. 9 is a schematic view of an exemplary alternative thermal desorption device 620 that may be used with sample system 200 (shown in FIGS. 2 and 4). Device 620 is substantially similar to device 600 (shown in FIG. 8) with the exception that device 620 is configured and oriented to supply a heated, pressurized gas flow (not shown) to array of samples 343 deposited on translatable sample substrate 342. In the exemplary embodiment, the gas used with device 600 is ambient air. Alternatively, any gas that enables operation of device 620 and sampling system 200 as described herein is used. Some alternative embodiments of thermal desorption device 620 include other fluid delivery means, including, without limitation, dopant delivery devices such as pump 233, transfer line 234, reservoir 235, and delivery line 236 (all shown in FIG. 2) integrated with heating element 603 and tube 604. Other alternative embodiments include APPI device 230 (shown in FIG. 2) used in addition to thermal desorption device 620.

Figure 10:
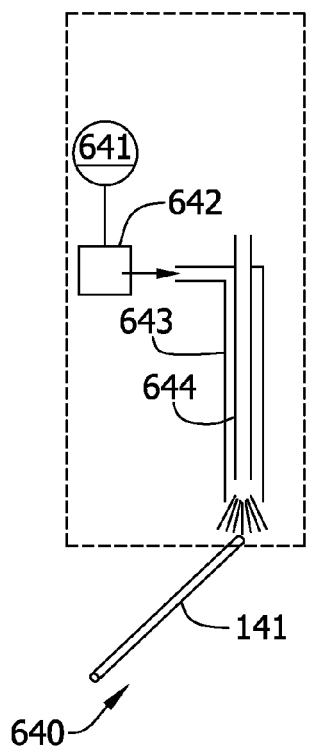
FIG. 10 is a schematic view of an exemplary nebulizer/vaporizer device that may be used with the sample system shown in FIGS. 2 and 4.

FIG. 10 is a schematic view of an exemplary nebulizer/vaporizer device 640 that may be used with sample system 200 (shown in FIGS. 2 and 4). Many commercial mass spectrometer systems have atmospheric pressure ionizers and generally have a means to provide a heated gas flow for nebulization and vaporization of a liquid sample flow from sources such as liquid chromatography. Nebulizer/vaporizer device 640 includes a gas source 641 coupled in flow communication with a gas pump 642, a gas conduit 643 coupled in flow communication with pump 642, and a gas tube 644 inserted with gas conduit 643. Heated gas flow (not shown) is provided by gas source 641 and pump 642 through conduit 643. In the exemplary embodiment, the gas used with device 640 is ambient air. Alternatively, any gas that enables operation of device 640 and sampling system 200 as described herein is used.

Liquid chromatography capillary 141 is inserted into tube 644. For the purposes of achieving ambient analysis by APPI device 230 (shown in FIG. 2) using a conventional nebulizer/vaporizer, the heated gas flow through conduit 643 would suffice as the desorption gas flow for samples such as capillary tube 141. Some alternative embodiments of nebulizer/vaporizer device 640 include other fluid delivery means, including, without limitation, dopant delivery devices such as pump 233, transfer line 234, reservoir 235, and delivery line 236 (all shown in FIG. 2) integrated with tube 644. Other alternative embodiments include APPI device 230 (shown in FIG. 2) used in addition to nebulizer/vaporizer device 640.

Figure 11:
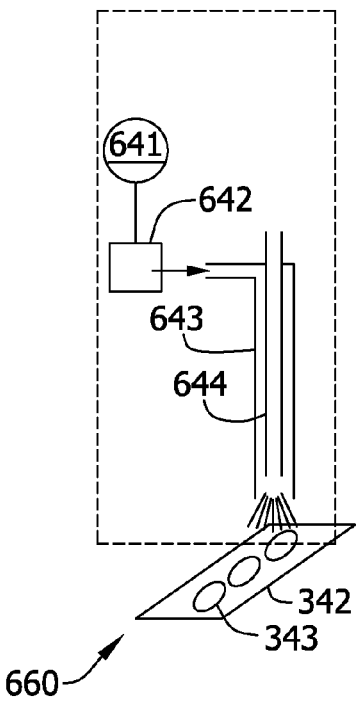
FIG. 11 is a schematic view of an exemplary alternative nebulizer/vaporizer device that may be used with the sample system shown in FIGS. 2 and 4.

FIG. 11 is a schematic view of an exemplary alternative nebulizer/vaporizer device 660 that may be used with sample system 200 (shown in FIGS. 2 and 4). Device 660 is substantially similar to device 640 (shown in FIG. 10) with the exception that device 660 is configured and oriented to supply a heated, pressurized gas flow (not shown) to array of samples 343 deposited on translatable sample substrate 342. In the exemplary embodiment, the gas used with device 660 is ambient air. Alternatively, any gas that enables operation of device 660 and sampling system 200 as described herein is used. Some alternative embodiments of nebulizer/vaporizer device 660 include other fluid delivery means, including, without limitation, dopant delivery devices such as pump 233, transfer line 234, reservoir 235, and delivery line 236 (all shown in FIG. 2) integrated with tube 644. Other alternative embodiments include APPI device 230 (shown in FIG. 2) used in addition to nebulizer/vaporizer device 660.

Figure 12:
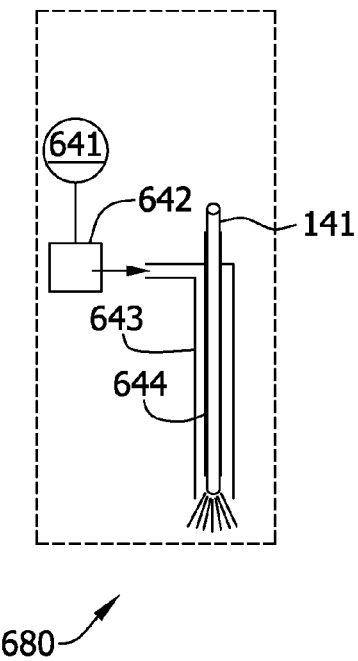
FIG. 12 is a schematic view of another exemplary alternative nebulizer/vaporizer device that may be used with the sample system shown in FIGS. 2 and 4.

FIG. 12 is a schematic view of another exemplary alternative nebulizer/vaporizer device 680 that may be used with sample system 100 (shown in FIGS. 2 and 4). Nebulizer/vaporizer device 680 is similar to device 640 (shown in FIG. 10) with the exception that capillary sample tube 141 is inserted into gas tube 644 such that capillary sample tube 141 is coaxial with the gas flow (not shown in FIG. 12). Such configuration facilitates a convenient means to perform rapid and efficient sample analysis.

Figure 13:
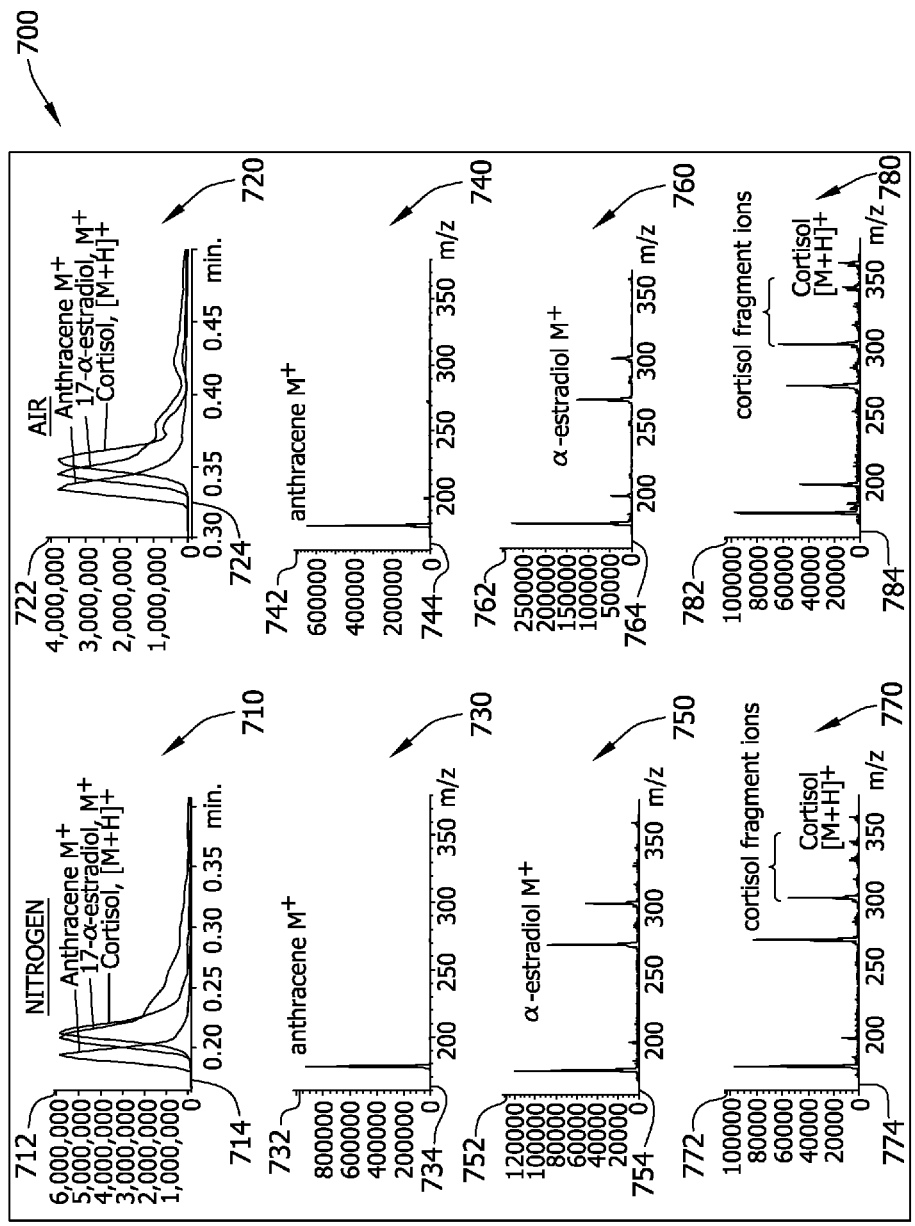
FIG. 13 is a plurality of related graphical views of analysis results using nitrogen and air with the nebulizer/vaporizer devices shown in FIGS. 10 and 11.

FIG. 13 is a plurality of related graphical views, i.e., graphs 700 of analysis of results using nitrogen and air with nebulizer/vaporizer device 640 (shown in FIG. 10). Graphs 700 include a first graph 710 and a second graph 720 that show a time dependence for desorption and ionization of three test compounds, i.e., anthracene, α-estradiol, and cortisol, when capillary 141 (shown in FIG. 10) is inserted into the hot gas flow generated by nebulizer/vaporizer device 640. First graph 710 and second graph 720 represent use of heated pure nitrogen and ambient air, respectively. All three compounds are deposited on capillary 141 together for simultaneous analysis under both the nitrogen and ambient air scenerios.

Graph 710 includes an ordinate (y-axis) 712 that represents a total ion count, wherein such values at least partially represent a relative abundance of the constituents of the compound under analysis. Y-axis 712 is shown in ion count increments of 1,000,000 from 0 to 6,000,000. Graph 710 also includes an abscissa (x-axis) 714 that represents time from approximately 0.15 minutes to 0.40 minutes. As shown in graph 710, desorption of each of anthracene, α-estradiol, and cortisol occurs very rapidly and completely when exposed to the heated nitrogen flow from nebulizer/vaporizer device 640.

Graph 720 includes an ordinate (y-axis) 722 that represents a total ion count, wherein such values at least partially represent a relative abundance of the constituents of the compound under analysis. Y-axis 722 is shown in ion count increments of 500,000 from 0 to 4,000,000. Graph 720 also includes an abscissa (x-axis) 724 that represents time from approximately 0.30 minutes to 0.50 minutes. As shown in graph 720, desorption of each of anthracene, α-estradiol, and cortisol occurs very rapidly and completely when exposed to the heated ambient air flow from nebulizer/vaporizer device 640.

Graphs 700 also include mass spectra graphs 730 and 740 for anthracene exposed to heated nitrogen and air, respectively. Graph 730 includes an ordinate (y-axis) 732 that represents a signal amplitude in unitless values that at least partially represent a relative abundance of the constituents of the compound under analysis. Y-axis 732 is shown in increments of 50,000 from 0 to 1,000,000. Graph 730 also includes an abscissa (x-axis) 734 that represents a dimensionless mass-to charge (m/z) ratio along a spectrum generated by the compound under analysis. X-axis 734 is shown in increments of 10 from 150 through 380. The molecular ion peak $M^+$ value is approximately 929,152.

Graph 740 includes an ordinate (y-axis) 742 that represents a signal amplitude in unitless values that at least partially represent a relative abundance of the constituents of the compound under analysis. Y-axis 742 is shown in increments of 20,000 from 0 to 700,000. Graph 740 also includes an abscissa (x-axis) 744 that represents a dimensionless mass-to charge (m/z) ratio along a spectrum generated by the compound under analysis. X-axis 744 is shown in increments of 10 from 150 through 380. The molecular ion peak $M^+$ value is approximately 649,216. A comparison of graphs 730 and 740 indicate that use of inexpensive ambient air generates similar results to that of expensive, and cumbersome, pure nitrogen for analysis of anthracene.

Graphs 700 also include mass spectra graphs 750 and 760 for α-estradiol exposed to heated nitrogen and air, respectively. Graph 750 includes an ordinate (y-axis) 752 that represents a signal amplitude in unitless values that at least partially represent a relative abundance of the constituents of the compound under analysis. Y-axis 752 is shown in increments of 5,000 from 0 to 120,000. Graph 750 also includes an abscissa (x-axis) 754 that represents a dimensionless mass-to charge (m/z) ratio along a spectrum generated by the compound under analysis. X-axis 754 is shown in increments of 10 from 150 through 380. The molecular ion peak M⁺ value is approximately 199,560.

Graph 760 includes an ordinate (y-axis) 762 that represents a signal amplitude in unitless values that at least partially represent a relative abundance of the constituents of the compound under analysis. Y-axis 762 is shown in increments of 10,000 from 0 to 300,000. Graph 760 also includes an abscissa (x-axis) 764 that represents a dimensionless mass-to charge (m/z) ratio along a spectrum generated by the compound under analysis. X-axis 764 is shown in increments of 10 from 150 through 380. The molecular ion peak M⁺ value is approximately 278,080. A comparison of graphs 750 and 760 indicate that use of inexpensive ambient air generates similar results to that of expensive, and cumbersome, pure nitrogen for analysis of α-estradiol.

Graphs 700 also include mass spectra graphs 770 and 780 for cortisol exposed to heated nitrogen and air, respectively. Graph 770 includes an ordinate (y-axis) 772 that represents a signal amplitude in unitless values that at least partially represent a relative abundance of the constituents of the compound under analysis. Y-axis 772 is shown in increments of 5,000 from 0 to 120,000. Graph 770 also includes an abscissa (x-axis) 774 that represents a dimensionless mass-to charge (m/z) ratio along a spectrum generated by the compound under analysis. X-axis 774 is shown in increments of 10 from 150 through 380. The molecular ion peak M⁺ value is approximately 97,624.

Graph 780 includes an ordinate (y-axis) 782 that represents a signal amplitude in unitless values that at least partially represent a relative abundance of the constituents of the compound under analysis. Y-axis 782 is shown in increments of 5,000 from 0 to 300,000. Graph 780 also includes an abscissa (x-axis) 784 that represents a dimensionless mass-to charge (m/z) ratio along a spectrum generated by the compound under analysis. X-axis 784 is shown in increments of 10 from 150 through 380. The molecular ion peak M⁺ value is approximately 97,624. A comparison of graphs 770 and 780 indicate that use of inexpensive ambient air generates similar results to that of expensive, and cumbersome, pure nitrogen for analysis of cortisol.

Figure 14:
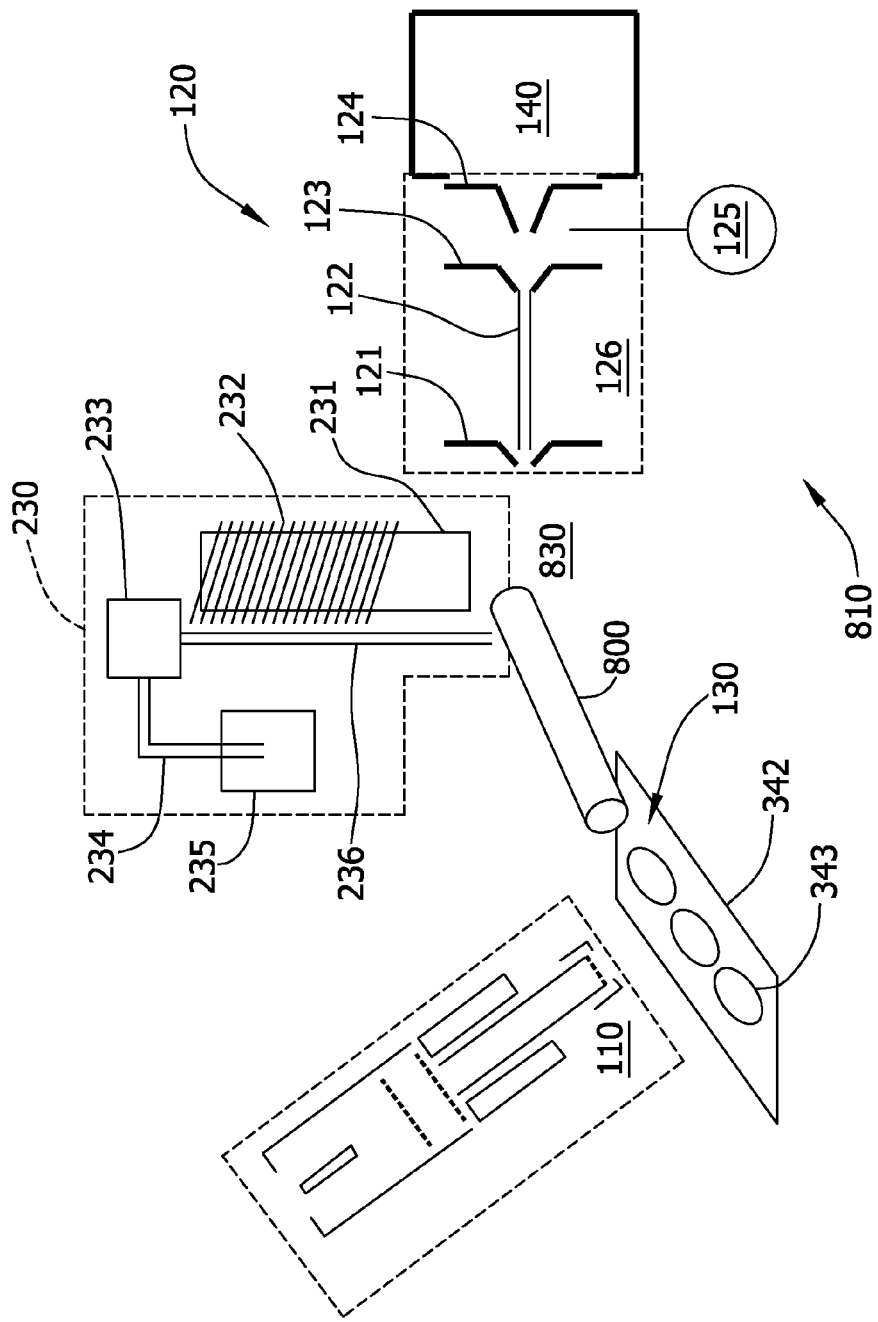
FIG. 14 is a schematic view of the sampling system shown in FIG. 3 with an exemplary transfer tube.
Figure 15:
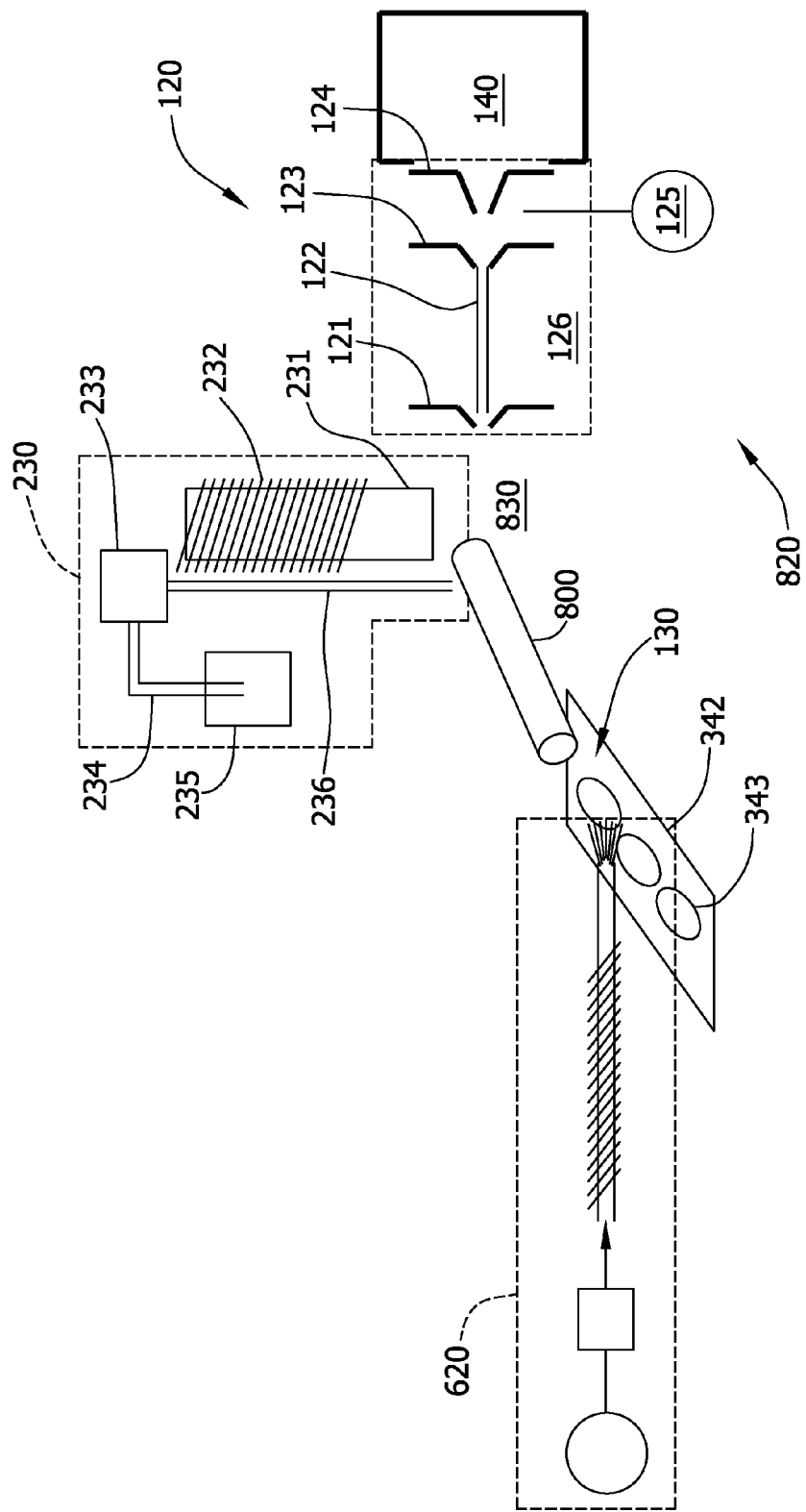
FIG. 15 is a schematic view of the sampling system shown in FIG. 15 with the DART device replaced by the thermal desorption device shown in FIGS. 8 and 9.

FIG. 14 is a schematic view of sampling system 300 with an exemplary transfer tube 800, thereby defining an alternative sampling system 810. FIG. 15 is a schematic view of sampling system 810 (shown in FIG. 14) with DART device 110 (shown in FIG. 14) replaced by thermal desorption device 620, thereby defining another alternative sampling system 820. Both alternative sampling systems 810 and 820 include transfer tube 800 for directing desorbed vapors to APPI device 230, wherein transfer tube 800 is positioned proximate to sampling region 130 and at least partially defines an ionization region 830 in close proximity to ion vacuum interface 126.

As shown in FIG. 14, sampling system 810 uses DART device 110 as the desorbing source and as shown in FIG. 15, the desorbing source is thermal desorption device 620. The benefit of transfer tube 800 is that it allows thermal desorption to occur at locations somewhat distant from the ion vacuum interface 126 while performing ionization by APPI 230 close to ion vacuum interface 126, thereby retaining high efficiency for sampling ions into high vacuum ion mass analyzer 140. Moreover, such sampling systems 810 and 820 facilitate large and/or uniquely and/or cumbersomely configured samples, or an array of a plurality of samples that cannot be brought close to ion vacuum interface 126.

In the exemplary alternative embodiments, sampling systems 810 and 820 separate the steps of thermal desorption and ionization. Therefore, transfer tube 800 transfers neutral sample vapor and not ions, thereby facilitating an efficiency of neutral sample transfers through a sampling tube over an efficiency of a configuration that includes the transfer of ions. Also, since neutral samples are less reactive than ions, the effectiveness of the exemplary alternative embodiments including sampling systems 810 and 820 is improved by decreasing the number of ions in the neutral sample vapor being analyzed. In general, it is better to perform ionization as close to ion vacuum interface 126 as possible.

In order for transfer tube 800 to transfer desorbed vapors efficiently, a flow of gas is induced through tube 800. This is accomplished using desorption gas flow from either DART device 110 or thermal desorption device 620. The angle of flow from devices 110 and/or 620 may be adjusted to improve the forced flow through the transfer tube 800. For certain applications it might be beneficial to enclose sample region 130 in order to contain the gas flow and facilitate directing the flow through transfer tube 800. Some alternative embodiments of sampling systems 810 and 820 include apparatus (not shown) to channel the dopant flow from APPI 230 directly into sample transfer tube 800 by coupling dopant delivery line 236 to tube 800. Also, some alternative embodiments of sampling systems 810 and 820 include apparatus (not shown) to channel dopant flow from APPI 230 directly into the heated gas in sample region 130 through DART device 110 or thermal desorption device 620.

In the exemplary embodiment, direct, or active heating is not needed because the dopant flow discharged from APPI 230 is effectively vaporized by the heated metastable gas channeled from DART device 110 or thermal desorption device 620.

Figure 16:
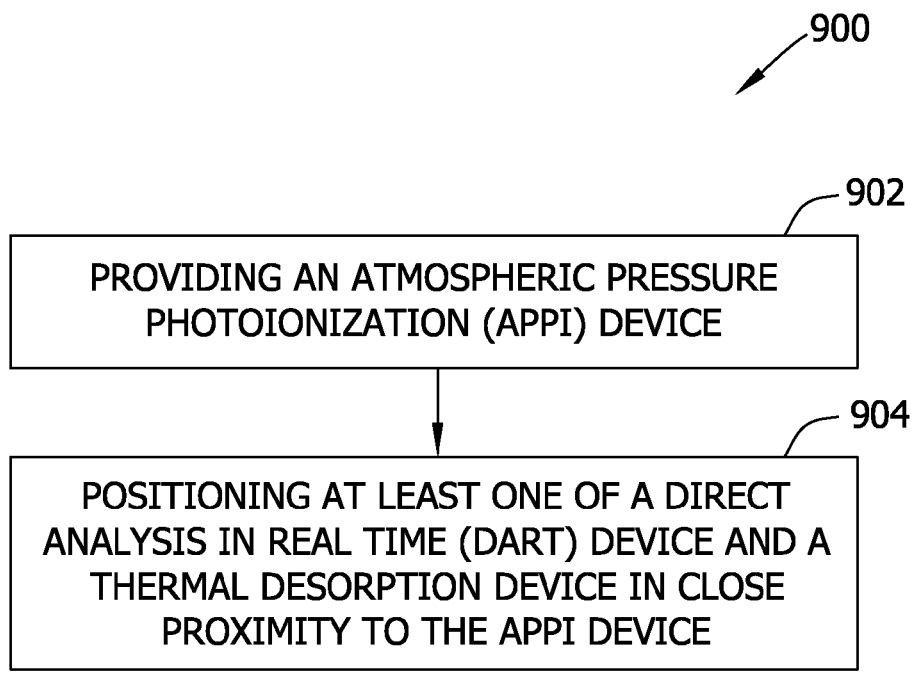
FIG. 16 is a flowchart of an exemplary method of assembling the sampling systems shown in FIGS. 2, 3, 14, and 15.

FIG. 16 is a flowchart of an exemplary method 900 of assembling sampling systems 200 (shown in FIG. 2), 300 (shown in FIG. 3), 810 (shown in FIG. 14), and 820 (shown in FIG. 15). Method 900 includes providing 902 atmospheric pressure photoionization (APPI) device 230 (shown in FIGS. 2, 3, 4, 14, and 15. Method 900 also includes positioning 904 at least one of a direct analysis in real time (DART) device (shown in FIGS. 2, 3, 4, and 14) and a thermal desorption device 600, 620 (shown in FIGS. 8 and 9, respectively), in close proximity of APPI device 230.

The above-described embodiments provide an ambient analysis sampling and detection system that enables direct chemical analysis in real time of samples either in their natural environment or deposited on object surfaces and/or convenient sample substrates. For example, some of the embodiments of sampling systems described herein enhance the performance of DART by adding an APPI device, an associated dopant flow, and predetermined geometric constraints to form desired ions and facilitate their transmission into an ion analyzer, such as a mass spectrometer. In such sampling systems, DART and APPI are combined to increase the effectiveness of DART-based sampling systems in detecting and analyzing a greater number of substances and/or compounds. Integration of APPI with DART significantly increases a sampling system-generated ionization signal relative to DART alone, and APPI is significantly less subject to charge affinities or the suppression effects of ion-molecule reactions. Other embodiments of sampling systems described herein do not use DART and instead use a heated gas flow to desorb the sample and then use APPI to ionize the vaporized neutral analyte sample, wherein both may use air rather than purified cylinder gases, thereby improving operational convenience for in-field use and reducing the costs of procuring and storing such purified cylinder gases. The use of air rather than more costly and operationally inconvenient purified gases for DART alone is facilitated by the beneficial physical properties of the APPI apparatus and associated methods as described herein.

Exemplary embodiments of chemical sampling and analysis systems are described above in detail. The methods and systems are not limited to the specific embodiments described herein, but rather, components of systems and/or steps of the methods may be utilized independently and separately from other components and/or steps described herein. For example, the methods may also be used in combination with other chemical sampling and analysis systems and methods, and are not limited to practice with only the systems and methods as described herein. Rather, the exemplary embodiment can be implemented and utilized in connection with many other chemical sampling and analysis systems and applications.

Although specific features of various embodiments of the invention may be shown in some drawings and not in others, this is for convenience only. In accordance with the principles of the invention, any feature of a drawing may be referenced and/or claimed in combination with any feature of any other drawing. Moreover, while certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A chemical sampling system comprising:
   a direct analysis in real time (DART) device;
   an atmospheric pressure photoionization (APPI) device positioned proximate to said DART device; and
   a transfer tube positioned between a sample region and said APPI device, said transfer tube oriented to channel a heated metastable gas stream including sample vapors from the sample region to an ionization region at least partially defined by said transfer tube, wherein said APPI device is coupled in flow communication with said DART device such that said APPI device is configured to channel a dopant flow into the heated metastable gas stream proximate the sample region prior to being channeled into said transfer tube.

2. A chemical sampling system in accordance with claim 1, wherein said DART device is coupled to a gas source comprising at least one of a helium source, an argon source, and a nitrogen source.

3. A chemical sampling system in accordance with claim 1 further comprising an ion detection device comprising:
   a mass spectrometer; and
   an ion sampling tube coupled in flow communication with said mass spectrometer, said ion sampling tube oriented and configured to receive at least a portion of the heated metastable gas stream and the dopant stream.

4. A chemical sampling system in accordance with claim 1, wherein said APPI device comprises a dopant source.

5. A chemical sampling system in accordance with claim 4, wherein the dopant stream is not actively heated prior to discharge from said APPI device.

6. A chemical sampling system in accordance with claim 4, wherein:
   said DART device is configured to generate the heated metastable gas stream; and
   said APPI device is oriented and configured to generate the dopant stream that intersects the heated metastable gas stream.

7. A chemical sampling system in accordance with claim 6, wherein said DART device is oriented at a predetermined angle to said APPI device.

8. A chemical sampling system in accordance with claim 1 further comprising one of:
   at least one sample positioned on a capillary tube;
   at least one sample positioned on a substrate; and
   a liquid sample stream.

9. A chemical sampling system in accordance with claim 1 further comprising a thermal desorption device positioned proximate to said DART device and said APPI device, said thermal desorption device comprising at least one of:
   a gas source; and
   at least one dopant source.

10. A chemical sampling system in accordance with claim 9, wherein said thermal desorption device further comprises at least one of a blower and a pump.

11. A chemical sampling system in accordance with claim 9, wherein said gas source comprises an air source.

12. A chemical sampling system in accordance with claim 1, wherein said APPI device is coupled in flow communication with said transfer tube such that said APPI device is configured to channel the dopant flow into the heated metastable gas stream including sample vapors within said transfer tube.

13. A chemical sampling system comprising:
   a thermal desorption device;
   an atmospheric pressure photoionization (APPI) device positioned proximate to said thermal desorption device; and
   a transfer tube positioned between a sample region and said thermal desorption device, said transfer tube oriented to channel a heated gas stream including sample vapors from the sample region to an ionization region at least partially defined by said transfer tube, wherein said APPI device is coupled in flow communication with said thermal desorption device such that said APPI device is configured to channel a dopant flow into the heated gas stream proximate the sample region prior to being channeled into said transfer tube.

14. A chemical sampling system in accordance with claim 13, wherein said thermal desorption device is configured to discharge a heated gas stream therefrom and said APPI device is configured to channel the dopant stream into the heated gas stream, wherein the dopant stream is not actively heated prior to discharge from said APPI device and the dopant is at least partially vaporized in the heated gas stream.

15. A chemical sampling system in accordance with claim 13, wherein said thermal desorption device is oriented at a predetermined angle to said APPI device.

16. A chemical sampling system in accordance with claim 13 further comprising one of:
   at least one sample positioned on capillary tube;
   at least one sample positioned on a substrate; and
   a liquid sample stream.

17. A chemical sampling system in accordance with claim 13, wherein said thermal desorption device comprises at least one of a blower and a pump.

18. A chemical sampling system in accordance with claim 13, wherein said thermal desorption device comprises an air source.

19. A chemical sampling system in accordance with claim 13, wherein said APPI device is coupled in flow communication with said transfer tube such that said APPI device is configured to channel the dopant flow into the heated gas stream including sample vapors within said transfer tube.

20. A method of assembling a chemical sampling system, said method comprising:
providing an atmospheric pressure photoionization (APPI) device;
positioning at least one of a direct analysis in real time (DART) device and a thermal desorption device in close proximity of the APPI device;
positioning a transfer tube between a sample region and the APPI device;
orienting the transfer tube to channel a heated gas stream including sample vapors from the sample region to an ionization region at least partially defined by the transfer tube; and
coupling the APPI device in flow communication with at least one of the DART device and the thermal desorption device such that the APPI device is configured to channel a dopant stream into the heated gas stream proximate the sample region prior to being channeled into the transfer tube.

21. A method in accordance with claim 20 further comprising orienting at least one of the DART device and the thermal desorption device to channel the heated gas stream with respect to the dopant stream discharged by the APPI device such that the heated gas stream and the dopant stream intersect.

22. A method in accordance with claim 21, wherein orienting at least one of the DART device and the thermal desorption device comprises orienting at least one of the DART device and the thermal desorption device at a predetermined angle with respect to the APPI device.

23. A method in accordance with claim 20 further comprising positioning a sample source in flow communication with the heated gas stream, wherein the sample source is one of:
a capillary tube;
a substrate; and
a liquid sample stream.

24. A method in accordance with claim 20 further comprising coupling the APPI device in flow communication with the transfer tube such that the APPI device is configured to channel the dopant flow into the heated gas stream including sample vapors within the transfer tube.

* * * * *